United States Patent [19]

Tanaka et al.

[11] 4,434,166

[45] Feb. 28, 1984

[54] ANIMAL COCCIDIOSIS PREVENTIVE

[75] Inventors: Ichiro Tanaka, Kodaira; Hiroshi Arato, Kagoshima; Takaaki Wakabayashi, Kamakura, all of Japan

[73] Assignee: Eisai Co., Ltd., Tokyo, Japan

[21] Appl. No.: 459,914

[22] Filed: Jan. 21, 1983

[30] Foreign Application Priority Data

Jan. 28, 1982 [JP] Japan ................................. 57-11020
Nov. 16, 1982 [JP] Japan ................................ 57-199687

[51] Int. Cl.³ ........................................... A61K 31/495
[52] U.S. Cl. ................................... 424/250; 424/353
[58] Field of Search ......................................... 424/250

[56] References Cited

PUBLICATIONS

Chem. Abst. 9 Collect Index vol. 76-85 (1972-1976) p. 14285cs.
Chem. Abst. 10th Collect Index vol. 86-95 (1977-1981) p. 19258cs.

*Primary Examiner*—Sam Rosen
*Attorney, Agent, or Firm*—Flynn, Thiel, Boutell & Tanis

[57] ABSTRACT

Animal coccidiosis can be effectively treated with a quinoxaline compound of the formula given below, alone or in combination with o-dichlorobenzene, wherein the quinoxaline compound has the formula:

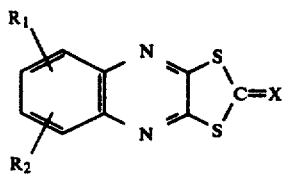

wherein $R_1$ and $R_2$ may be the same or different and each represent a hydrogen atom, lower alkyl group, halogen atom or lower alkoxy group and X represents an oxygen or sulfur atom.

17 Claims, No Drawings

ANIMAL COCCIDIOSIS PREVENTIVE

The present invention relates to a new animal coccidiosis preventive. More particularly, the invention relates to an animal coccidiosis preventive containing as an essential ingredient a quinoxaline derivative of the formula:

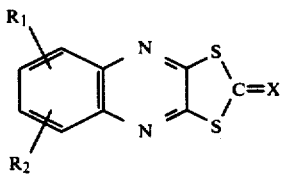

wherein $R_1$ and $R_2$ may be the same or different and each represents a hydrogen atom, lower alkyl group, halogen atom or lower alkoxy group and X represents an oxygen or sulfur atom. The invention further relates to an animal coccidiosis preventive composition which comprises (A) o-dichlorobenzene and (B) the quinoxaline compound as defined above.

Coccidiosis is a disease of domestic animals and poultry infected by a protistic parasite of the genus Eimeria. If they are infected with coccidiosis, diarrhea and hemorrhage are caused which tend to induce a nutrition disorder. Particularly, the damage is serious in chickens. For example, if chickens are infected with cecal coccidiosis, acute symptoms including hemorrhagic diarrhea are observed and fledgling chickens perish in several days. Therefore, poulterers are concerned about coccidiosis. Chicken small-intestine coccidiosis is chronic and is generally not fatal. However, since the parasite lives in the small intestine for a long period of time, it also causes a nutrition disorder and, accordingly, it is a highly damaging disease like cecal coccidiosis.

If a chicken takes in an oocyst, sporozoites are liberated in a digestive canal. The sporozoites immediately penetrate in the cells of the mucous membrane of the digestive canal and begin to propagate. After 1 or 2 days, they grow into a colony of the protozoa called schizont. Thereafter, their membranes are broken and several tens of merozoites come out and penetrate into the cells again. Several hours thereafter, the merozoites form schizont and propagate. At this time, the symptoms appear in the chicken. If the chicken survives this period, the disease takes a turn for the better and male and female protozoa are thus formed. After the fertilization, innumerable fresh oocysts are formed and discharged together with excrements and have a chance of infecting other chickens.

Methods of the treatment and prevention of coccidiosis due to the protozoa of the genus Eimeria may be roughly classified into those wherein a drug is administered orally to the animal to exterminate the pathogenoic protozoa and those wherein the excrements discharged from the animal's body are treated to exterminate the pathogenic protozoa, whereby the outbreak and spread of the animal coccidiosis are inhibited.

Investigations have been made for a long period of time and numerous drugs to be administered orally to the chickens have been developed. However, it is hardly expected that the oocysts can be wholly prevented from being discharged together with excrements. Further, drugs having satisfactory effects have not been developed yet. As for drugs used in the above-mentioned, latter method (external treatment), there have been used inorganic compound such as ammonia or medicines containing o-dichlorobenzene (one of the constituents of the present invention) as the principal ingredient together with, if necessary, phenol, cresol, a halocresol or sulfocresol. However, these drugs still have a problem of unsatisfactory oocysticidal effects. Under these circumstances, the development of more excellent medicines has been demanded.

After intensive investigations on oocysticides made for a long period of time, the inventors have found that, unexpectedly, a composition containing, as essential ingredients, o-dichlorobenzene and a quinoxaline compound of general formula (I):

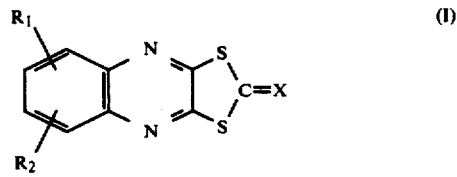

wherein $R_1$ and $R_2$ may be the same or different and each represent a hydrogen atom, lower alkyl group, halogen atom or lower alkoxy group and X represents an oxygen or sulfur atom, has a quite excellent oocysticidal effect. Namely, the inventors have found that an oocysticidal effect far superior to that obtained by using o-dichlorobenzene alone can be obtained by using a combination of o-dichlorobenzene with the above-mentioned quinoxaline compound. The present invention has been completed on the basis of this finding.

The present inventors have further discovered a method for treating an animal suffering from animal coccidiosis which comprises administering to the animal a therapeutically effective amount of a composition comprising the foregoing quinoxaline compound of the general formula (I). The composition used in this method may further include a therapeutically effective amount of o-dichlorobenzene.

An object of the present invention is to provide a new animal coccidiosis preventive composition having an excellent oocysticidal effect.

Another object of the invention is to provide a medicinal composition used externally for controlling the living environment of animals and exterminating pathogenic protozoa of the genus Eimeria to prevent the occurrence of animal coccidiosis.

Typical examples of quinoxaline compounds (I) used in the present invention are:
6-methyl-1,3-dithiolo[4,5-b]quinoxalin-2-one (Morestan),
6-methoxy-1,3-dithiolo[4,5-b]quinoxaline-2-thione,
1,3-dithiolo[4,5-b]quinoxaline-2-thione (Eraditon),
6-chloro-1,3-dithiolo[4,5-b]quinoxaline-2-thione,
1,3-dithiolo[4,5-b]quinoxalin-2-one,
5-methyl-1,3-dithiolo[4,5-b]quinoxalin-2-one and
5,7-dimethyl-1,3-dithiolo[4,5-b]quinoxalin-2-one.

The preventive of the present invention may be prepared in various forms such as powder, granules, wettable powder, emulsion, oil and fumigant. The emulsion is the most desirable form, since it exhibits the best effects.

The mixing ratio of o-dichlorobenzene to the quinoxaline compound is not particularly limited. Generally, however, preferred results are obtained with the ratio of about 40–95/0.1–15 (wt. %).

In the preparation of the emulsion, a surfactant most suitable for obtaining an emulsion stable in water may be used. If necessary, there may be incorporated also a solubilizer, penetrant, stabilizer, U.V. absorber and fixing agent therein. Further, phenol and substituted phenols such as cresol and xylenol may be used as oocysticide synergists or main solvents for the quinoxaline compounds.

Preferred surfactants are those having a high emulsion stability and adhesion which does not reduce the oocysticidal effects. As such a surfactant, there may be mentioned an anionic surfactant such as a carboxylic acid salt, sulfonic acid salt, sulfate ester salt or phosphate ester salt, a cationic surfactant such as a quaternary ammonium salt, pyrimidium salt or imidazolium salt, or amphoteric surfactant such as an aminocarboxylic acid salt, imidazoliumbetaine compound or carboxybetaine compound. However, with the above-mentioned ionic surfactant alone, a sufficient emulsion stability in water cannot be obtained in some cases. More concretely, the emulsion state is broken by metal ions such as alkali metal ions in excretions of animals and in the soil or by organic matter contained therein to make it impossible to obtain the intended effects. In addition, the local combination and concentration of o-dichlorobenzene and the quinoxaline compound occur in the subject to which the drug has been applied. Particularly when the subject is excrement of an animal such as fowl droppings, the crops will be badly damaged by the drug if the fowl droppings are used as a fertilizer. This damage can be avoided by selecting an optimum nonionic surfactant and using it in combination with the above-described ionic surfactant. As examples of the nonionic surfactants, there may be mentioned polyoxyethylene alkyl ethers, polyoxyethylene alkylaryl ethers and formalin condensates thereof, ether ester-type nonionic surfactants such as polyoxyethylene glycerol/fatty acid esters, polyoxyethylene/fatty acid ester-type nonionic surfactants and nitrogen-containing nonionic surfactants such as polyoxyethylene/fatty acid amides.

As the solubilizers, there may be mentioned, for example, ketones such as cyclohexanone and isophorone, ethers such as ethylene glycol monophenol ether, sulfolane ethylene carbonate, tetrahydrofuran, hexamethylphosphoramide, dimethyl sulfoxide, dimethylformamide and N-methylpyrrolidone.

As the penetrants, there may be mentioned, for example, alkyl sulfosuccinates. As the stabilizers, there may be mentioned acidic substances such as alkyl acid phosphates and polyhydric phenols, epoxy compounds such as epichlorohydrin and butyl glycidyl ether, and basic compounds such as alkanolamines, alkylamines and alkylaniline.

As the fixing agents, there may be mentioned, for example, oil-soluble resins, higher fatty acids and high molecular weight hydrocarbons. As the U.V. absorbers, there may be mentioned, for example, benzophenones, salicylic acid compounds such as ethylene glycol salicylate and cyanoacrylic compounds.

The following examples of the recipes and experiments will further illustrate the effects of the present invention. The examples of the recipes given below by no means limit the invention. In the following examples, percentages are given by weight.

EXAMPLE 1

| Recipe: | |
|---|---|
| o-Dichlorobenzene | 81 (%) |
| 6-Methyl-1,3-dithiolo[4,5-b]quinoxalin-2-one (Morestan) | 2 |
| Dimethyl sulfoxide | 5 |
| Surfactant | 12 |
| Polyoxyethylene (addition mol number: 16–20) octylphenyl ether | 50 |
| Polyoxyethylene (addition mol number: 50) castor oil | 20 |
| Calcium dodecylbenzenesulfonate | 30 |
| Total | 100 (%) |

An emulsion was prepared according to the above recipe by an ordinary method.

EXAMPLE 2

| Recipe: | |
|---|---|
| o-Dichlorobenzene | 85 (%) |
| 1,3-Dithiolo[4,5-b]quinoxaline-2-thione | 2 |
| Dimethyl sulfoxide | 5 |
| Surfactant | 8 |
| Polyoxyethylene (addition mol number: 16–20) octyphenyl ether | 50 |
| Polyoxyethylene (additon mol number: 50) castor oil | 20 |
| Calcium dodecylbenzenesulfonate | 30 |
| Total | 100 (%) |

An emulsion was prepared according to the above recipe by an ordinary method.

EXAMPLE 3

| Recipe: | |
|---|---|
| o-Dichlorobenzene | 75% |
| 1,3-Dithiolo[4,5-b]quinoxalin-2-one | 5 |
| m-Cresol | 5 |
| Surfactant | 15 |
| Polyoxyethylene (addition mol number: 16–14) nonylphenyl ether | 40 |
| Dioctyl sulfosuccinate | 20 |
| Polyoxyethylene (addition mol number: 12–14) styrylphenyl ether | 15 |
| Calcium dodecylbenzenesulfonate | 25% |

An emulsion was prepared according to the above recipe by an ordinary method.

EXAMPLE 4

| Recipe: | |
|---|---|
| o-Dichlorobenzene | 62 (%) |
| 5-Methyl-1,3-dithiolo[4,5-b]quinoxalin-2-one | 3 |
| 3,5-Xylenol | 5 |
| Benzalkonium chloride | 10 |
| Polyoxyethylene (addition mol number: 13) nonylphenyl ether | 15 |
| Ethanol | 5 |

An emulsion was prepared according to the above recipe by an ordinary method.

EXAMPLE 5

| Recipe: | |
|---|---|
| o-Dichlorobenzene | 82 |
| 6-Chloro-1,3-dithiolo[4,5-b]quinoxaline-2-thione | 3 |
| Dimethylformamide | 5 |
| Surfactant | 10 |
| Polyoxyethylene (addition mol number: 16-20) dodecylphenyl ether | 40 |
| Polyoxyethylene (addition mol number: 50) castor oil | 30 |
| Calcium dodecylbenzenesulfonate | 30 |

An emulsion was prepared according to the above recipe by an ordinary method.

EXAMPLE 6

| Recipe: | |
|---|---|
| o-Dichlorobenzene | 77 (%) |
| 5,7-Dimethyl-1,3-dithiolo[4,5-b]-quinoxalin-2-one | 5 |
| N—Methylpyrrolidone | 8 |
| Surfactant | 10 |
| Polyoxyethylene (addition mol number: 16-20) styrylphenyl ether/formalin polymer (n = 3) | 60 |
| Calcium dodecylbenzenesulfonate | 40 |

An emulsion was prepared according to the above recipe by an ordinary method.

EXAMPLE 7

| Recipe: | |
|---|---|
| o-Dichlorobenzene | 85 |
| 6-Methoxy-1,3-dithiolo[4,5-b]quinoxalin-2-one | 5 |
| Benzethonium chloride | 3 |
| Isopropyl alcohol | 3 |
| Polyoxyethylene (addition mol number: 16-20) phenylphenol ether | 4 |

An emulsion was prepared according to the above recipe by an ordinary method.

EXAMPLE 8

| Recipe: | |
|---|---|
| 6-Methyl-1,3-dithiolo[4,5-b]quinoxalin-2-one (Morestan) | 3 |
| xylene | 80 |
| Surfactant | 12 |
| Polyoxyethylene (addition mol number: 16-20) octylphenyl ether | 50 |
| Polyoxyethylene (addition mol number: 50) castor oil | 20 |
| Calcium dodecylbenzenesulfonate | 30 |
| Total | 100 (%) |

An emulsion was prepared according to the above recipe by an ordinary method.

EXAMPLE 9

An emulsion was obtained in the same manner as shown in Example 8 except that 1,3-dithiolo[4,5-b]quinoxalin-2-thione (ellagitone) was used instead of 6-methyl-1,3-dithiolo[4,5-b]quinoxalin-2-one.

The following test results show the effects of the present invention:

TESTS

Antisporulation effects against *Eimeria tenella* oocysts

1. Test method:

(1) Oocysticidal effects of samples having the compositions shown in Examples 1 to 9 against immature oocysts of *Eimeria tenella* were examined. As Control 1, "Ortho-zai" (comprising 70% of o-dichlorobenzene, 10% of m-cresol, 5% of ethanol and 15% of castor oil sulfate salt) used generally as an oocysticide was used. As Control 2, an agent comprising 90 wt. % of o-dichlorobenzene and 10 wt. % of an emulsifier was used.

(2) 50,000 *Eimeria tenella* oocysts were given orally to each young male white leghorn (Goto 360; one week old) raised under coccidium-free conditions. After 8 days, the chickens were sacrificed and their ceca were taken out. Oocysts were collected from the contents of each cecum and suspended in distilled water. The resulting suspension was subjected to the test. The number of oocysts subjected to the test was $10^7$ to $10^8$.

(3) The sample was diluted to a concentration of 1/200 with distilled water. 3 ml of the diluted sample and 3 ml of the oocyst suspension were placed in a Petri dish, mixed well and left to stand at 24° to 26° C. By the above-mentioned procedure, the oocysts were treated with 1/400 concentration of the sample. Two hours after, the mixture was transferred to a centrifugal tube, to which was added a 0.5% solution of Lipon (Lipon F; a product of Lion Yushi Co., Ltd.). The resulting solution was stirred well and centrifuged (400 g) for 5 min. The supernatat liquid was removed and the precipitate was again suspended in the Lipon solution and centrifuged to remove the sample. In each test, the centrifugation was repeated 5 times for removing the sample. After removing the sample by washing, the oocysts were suspended in 10 ml of a potassium dichromate solution. The suspension was transferred into a Petri dish and cultured at about 25° to 28° C.

(4) Observation and judgement:

After the culture for 4 to 5 days, a small quantity of the culture liquid was placed on a slide glass and then a cover glass was placed thereon.

In the microscopic observation, more than 200 immature and mature oocysts were counted.

The sporulation rate was represented by a percentage of the mature oocysts based on the total number of the oocysts counted. The lower the sporulation rate, the more excellent the effect of the sample. The sporulation rate of the sample was judged by the significance test as compared with that of the control.

2. Test results

The test results are shown in Table 1.

TABLE 1

| Sample | Sporulation rate (%) |
|---|---|
| Ex. 1 | 0 |
| Ex. 2 | 0 |
| Ex. 3 | 0 |
| Ex. 4 | 0 |
| Ex. 5 | 0 |
| Ex. 6 | 0 |
| Ex. 7 | 0 |
| Control 1 | 65.5 |
| Ex. 8 | 10.0 |
| Ex. 9 | 30.3 |

TABLE 1-continued

| Sample | Sporulation rate (%) |
| --- | --- |
| Control 2 | 59.4 |

It is apparent from Table 1 that sporulation rates of Examples 1 to 7 of the present invention were 0 and that they are far superior to the controls. Thus, the samples of the invention have far superior oocysticidal effects to that of "Ortho-zai" frequently used for treating animal coccidiosis in the prior art and the present invention is highly valuable.

The above mentioned Ortho-zai is a composition or mixture which contains ortho-dichlorobenzene.

The embodiments of the invention in which an exclusive property or privilege is claimed are defined as follows:

1. A method for treating an animal suffering from animal coccidiosis which comprises administering to said animal a therapeutically effective amount of a composition comprising a quinoxaline compound of the formula:

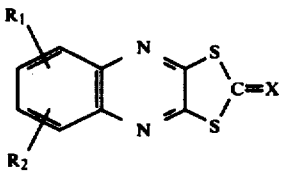

wherein $R_1$ and $R_2$ are the same or different and represent hydrogen, lower alkyl, halogen or lower alkoxy, and X represents oxygen or sulfur.

2. A method as claimed in claim 1, wherein said composition further comprises a therapeutically effective amount of o-dichlorobenzene.

3. A method as claimed in claim 1 in which said quinoxaline compound is selected from the group consisting of:
6-methyl-1,3-dithiolo[4,5-b]quinoxalin-2-one,
6-methoxy-1,3-dithiolo[4,5-b]quinoxaline-2-thione,
1,3-dithiolo[4,5-b]quinoxaline-2-thione,
6-chloro-1,3-dithiolo[4,5-b]quinoxaline-2-thione,
1,3-dithiolo[4,5-b]quinoxalin-2-one,
5-methyl-1,3-dithiolo[4,5-b]quinoxalin-2-one and
5,7-dimethyl-1,3-dithiolo[4,5-b]quinoxalin-2-one.

4. A method as claimed in claim 2 in which said quinoxaline compound is selected from the group consisting of:
6-methyl-1,3-dithiolo[4,5-b]quinoxalin-2-one,
6-methoxy-1,3-dithiolo[4,5-b]quinoxaline-2-thione,
1,3-dithiolo[4,5-b]quinoxaline-2-thione,
6-chloro-1,3-dithiolo[4,5-b]quinoxaline-2-thione,
1,3-dithiolo[4,5-b]quinoxalin-2-one,
5-methyl-1,3-dithiolo[4,5-b]quinoxalin-2-one and
5,7-dimethyl-1,3-dithiolo[4,5-b]quinoxalin-2-one.

5. A method for inhibiting sporulation of oocysts of pathogenic protozoa of the genus Eimeria, comprising treating said oocysts with an amount of a composition comprising a quinoxaline compound of the formula:

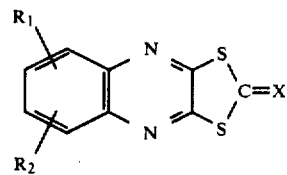

wherein $R_1$ and $R_2$ are the same or different and represent hydrogen, lower alkyl, halogen, or lower alkoxy, and X is oxygen or sulfur, effective to inhibit sporulation of said oocysts.

6. A method as claimed in claim 5, wherein said composition further comprises o-dichlorobenzene.

7. A method as claimed in claim 6, wherein said composition contains 40 to 95 wt. % of o-dichlorobenzene and 0.1 to 15 wt. % of said quinoxaline compound.

8. A method as claimed in claim 7, wherein said composition is an emulsion consisting essentially of said o-dichlorobenzene, said quinoxaline compound, a surfactant, at least one additive selected from the group consisting of a solubilizer, a penetrant, a stabilizer, a U.V. absorber and a fixing agent, and the balance is water.

9. A method as claimed in claim 7, wherein said composition further contains an effective amount of an oocysticide synergist selected from the group consisting of substituted and unsubstituted phenols.

10. A method as claimed in claim 7, wherein said oocysts are present in animal excrement.

11. A method as claimed in claim 6, wherein said quinoxaline compound is selected from the group consisting of:
6-methyl-1,3-dithiolo[4,5-b]quinoxalin-2-one,
6-methoxy-1,3-dithiolo[4,5-b]quinoxaline-2-thione,
1,3-dithiolo[4,5-b]quinoxaline-2-thione,
6-chloro-1,3-dithiolo[4,5-b]quinoxaline-2-thione,
1,3-dithiolo[4,5-b]quinoxalin-2-one,
5-methyl-1,3-dithiolo[4,5-b]quinoxalin-2-one and
5,7-dimethyl-1,3-dithiolo[4,5-b]quinoxalin-2-one.

12. A method as claimed in claim 5, wherein said oocysts are of the species *Eimeria tenella*.

13. An oocysticidal composition comprising an effective amount of o-dichlorobenzene and an effective amount of a quinoxaline compound of the formula:

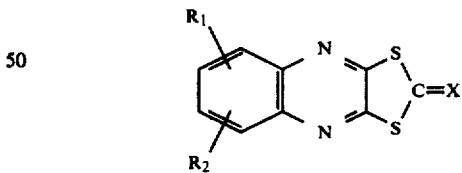

wherein $R_1$ and $R_2$ are the same or different and represent hydrogen, lower alkyl, halogen, or lower alkoxy, and X is oxygen or sulfur.

14. A composition as claimed in claim 13, in which said quinoxaline compound is selected from the group consisting of:
6-methyl-1,3-dithiolo[4,5-b]quinoxalin-2-one,
6-methoxy-1,3-dithiolo[4,5-b]quinoxaline-2-thione,
1,3-dithiolo[4,5-b]quinoxaline-2-thione,
6-chloro-1,3-dithiolo[4,5-b]quinoxaline-2-thione,
1,3-dithiolo[4,5-b]quinoxalin-2-one,
5-methyl-1,3-dithiolo[4,5-b]quinoxalin-2-one and
5,7-dimethyl-1,3-dithiolo[4,5-b]quinoxalin-2-one.

15. A composition as claimed in claim 13, wherein said composition contains from 40 to 95 wt. % of o-dichlorobenzene and from 0.1 to 15 wt. % of said quinoxaline compound.

16. A composition as claimed in claim 15, wherein said composition is an aqueous emulsion consisting essentially of said o-dichlorobenzene, said quinoxaline compound, a surfactant effective to form said emulsion in water, at least one additive selected from the group consisting of a solubilizer, a penetrant, a stabilizer, a U.V. absorber and a fixing agent, and the balance is essentially water.

17. A composition as claimed in claim 15, wherein said composition further contains an effective amount of an oocysticide synergist selected from the group consisting of substituted and unsubstituted phenols.

* * * * *